(12) United States Patent
Zanotti-Gerosa et al.

(10) Patent No.: US 6,613,922 B2
(45) Date of Patent: Sep. 2, 2003

(54) PHOSPHORUS P-CYCLOPHANE LIGANDS AND THEIR USE IN TRANSITION METAL CATALYZED ASYMMETRIC REACTIONS

(75) Inventors: Antonio Zanotti-Gerosa, Cambridge (GB); Christophe Guillaume Malan, Basel (CH); Julian Henschke, Cambridge (GB); Daniela Herzberg, Cambridge (GB)

(73) Assignee: Chirotech Technology Limited, Cambridge (GB)

( * ) Notice: Subject to any disclaimer, the term of this patent is extended or adjusted under 35 U.S.C. 154(b) by 0 days.

(21) Appl. No.: 10/055,069

(22) Filed: Jan. 22, 2002

(65) Prior Publication Data

US 2002/0151735 A1 Oct. 17, 2002

(30) Foreign Application Priority Data

Jan. 19, 2001 (GB) ............................... 0101461
Jan. 19, 2001 (GB) ............................... 0101462
Aug. 15, 2001 (GB) ............................... 0119955

(51) Int. Cl.$^7$ ................................. C07F 9/00
(52) U.S. Cl. ........................... 556/19; 558/73; 564/13; 568/12; 562/808
(58) Field of Search .............. 558/73, 76, 77, 558/78, 80, 81, 82, 83; 568/17, 12; 564/12, 13; 562/808, 811, 812; 556/13, 19; 560/125

(56) References Cited

U.S. PATENT DOCUMENTS 5,874,629 A  *  2/1999  Pye et al. ................... 568/17
6,486,337 B2 * 11/2002 Burk et al. .................. 556/22
2002/0026064 A1 * 2/2002 Burk et al. .................. 556/14

FOREIGN PATENT DOCUMENTS

WO    WO 97/47632 A    12/1997

OTHER PUBLICATIONS

Burk, Mark J., William Hems, Daniela Herzberg, Christophe Malan, Antonio Zanotti–Gerosa (Dec. 28, 2000) "A Catalyst for Efficient and Highly Enantioselective Hydrogenation of Aromatic, Heteroaromatic, and α, β–Unsaturated Ketones" *Organic Letters* 2(26):4173–4176.

Giernoth, Ralf et al., (Dec. 13, 2000) "PHIP Detection of a Transient Rhodium Dihydride Intermediate in the Homogeneous Hydrogenation of Dehydroamino Acids" *J. Am. Chem. Soc.* 122(49):12381–12382.

Pye, Philip J., Kai Rossen, Robert A. Reamer, R.P. Volante, Paul J. Reider (Jun. 18, 1998) "[2,2]Phanephos–Ruthenium(II) Complexes: Highly Active Asymmetric Catalysts for the Hydrogenation of β–Ketoester" *Tetrahedron Letters* 39(25):4441–4444.

Reetz, Manfred T., Andreas Gosberg, Richard Goddard, Suk–Hun Kyung (1998) "Diphosphonites as highly efficient ligands for enantioselective rhodium–catalyzed hydrogenation" *Cemical Cmmunications, Royal Society of Chemistry*, GB, No. 19, pp. 2077–2078.

Reetz, Manfred T. and Andreas Gosberg (Jun. 4, 1999) "New non–$C_2$–symmetric phosphine–phosphonites as ligands in asymmetric metal catalysis" *Tetrahedron: Asymmetry* 10(11):2129–2137.

Reetz, Manfred T. and Thorsten Sell (Aug. 12, 2000) "Rhodium–catalyzed enantioselective hydrogenation using chiral monophosphonite ligands" *Tetrahedron Letters* 41(33):6333–6336.

* cited by examiner

*Primary Examiner*—Jean F. Vollano

(57) ABSTRACT

Chiral di-phosphonites and phosphhours diamides based on the ps-ortho disubstituted p-cyclophane skeleton are good ligands for transition metals, notably rhodium, iridium and ruthenium. Preferably, the transition metals are linked to the ligands by a diene compound chosen from 2,5-Norbornadiene (NBD) and 1,5-Cyclooctadiene (COD).

38 Claims, No Drawings

PHOSPHORUS P-CYCLOPHANE LIGANDS AND THEIR USE IN TRANSITION METAL CATALYZED ASYMMETRIC REACTIONS

FIELD OF THE INVENTION

This invention relates to new bidentate phosphines, phosphonite, phosphonous diamide and phosphonoamidite ligands having a p-cyclophane backbone, precursors thereof, and their use as ligands for transition metal-catalysed asymmetric reactions, notably rhodium, iridium and ruthenium-catalysed hydrogenation of double bonds.

BACKGROUND OF THE INVENTION

At the heart of most asymmetric catalytic synthesis is the use of catalysts based on a transition metal surrounded by appropriate chiral, enantiomerically enriched, organic ligands. Bidentate chiral phosphines (phosphorus III compounds with three C—P bonds) are the most widely used class of ligands, finding applications in a range of asymmetric reactions (R. Noyori, *Asymmetric Catalysis in Organic Synthesis,* John Wiley & Sons, 1994; N. Jacobsen, A. Pfaltz, H. Yamamoto editors, *Comprehensive Asymmetric Catalysis,* Springer, 1999). Asymmetric catalytic hydrogenation has a particular industrial relevance because of its high efficiency and reduced environmental impact.

It has recently been shown that some of the results obtained with phosphines-based catalysts can be matched by the use of complexes where the phosphane ligands have been replaced by phosphonites (two P—O bonds and one P—C bond, Reetz et al, *Chem. Commun.* 1998, 2077), phosphine-phosphonites (Reetz et al, *Tetrahedron: Asymmetry* 1999, 2129) or phosphoramidites (two P—N and one P—O bond, Feringa et al, *J. Am. Chem. Soc.* 2000, 11539). Chiral monodentate phosphonites (Pringle et al, *Chem. Commun.* 2000, 961; Reetz et al, *Tetrahedron Lett.* 2000, 6333) and mono-phosphites (three P—O bonds, M. T. Reetz et al, *Angew. Chem. Int. Ed.* 2000, 3889) were often as effective as the analogous bidentate ligands. The above ligands often have the advantage of being easier and cheaper to prepare than the corresponding diphosphines.

Chiral bidentate phosphonites are disclosed in WO-00/14096 and U.S. Pat. No. 5817850. They are composed of three building blocks, i.e. an achiral carbon backbone (1,1'-disubstituted ferrocene, 1,2-disubstituted ethane) joining the two phosphorus atoms; and two chiral units derived from a chiral diol to form the P-heteroatom bonds. Examples of this class of ligands are described by Reetz et al, *Chem. Commun.* 1998, 2077).

Some phosphorus diamide ligands have been reported, and their complexes have been demonstrated to be useful in hydroformilation reactions and allylic substitutions (Wills et al, *J.Org.Chem.* 1999, 9735; Spilling et al. *Tetrahedron* 1998, 54, 10513; *Tetrahedron: Asymmetry* 1998, 927; Knochel et al. *Tetrahedron: Asymmetry* 1997, 987).

[2.2]-p-Cyclophane derivatives bearing two identical substituents at so-called pseudo-ortho positions (4- and 12-positions; abbreviated as ps-ortho) possess planar chirality. The successful diphosphine ligand PhanePhos (Pye et al, *J. Am. Chem. Soc.* 1997, 6207; WO 97/47632), is based on this skeleton.

SUMMARY OF THE INVENTION

According to one aspect of the present invention, a novel compound is ps-ortho-diphosphino-[2.2]-p-cyclophane (1)

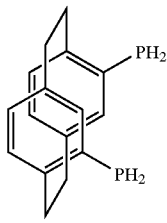

(1)

This compound is useful as a general intermediate that allows ready access to a range of cyclic phosphine ligands having application in asymmetric catalysis. Preferably, compound (1) is enriched to at least 80% ee in the enantiomer depicted (S) or in the opposite enantiomer (R). More preferably, it is enriched to 95% ee, or higher. Compound (1) may be prepared using the tetrachloro analogue described below as compound 4d.

Further, it has now been appreciated that by combining the structural features of PhanePhos ligands (the chiral backbone) with either DuPHOS or FerroTANE ligands (phosphine atoms in 4- or 5-membered saturated ring) hybrid ligands represented by general formulae (2) and (3) can be envisaged, wherein $R^1$ and $R^2$ represent H or alkyl and n is 1 or 2. To date, no ligand of this type has been described in the literature. Importantly, the presence of a chiral backbone allows a flexible approach to ligand design, since the cyclic phosphine units may either be chiral (e.g. $R^1$=methyl, $R^2$=H or vice versa), allowing catalyst tuning through a "matched" diastereomeric pairing, or achiral (e.g. $R^1$=$R^2$=H), allowing construction from inexpensive diols of the type HO—$(CH_2)_n$—OH. It cannot be readily predicted which of ligands (2) and (3) will have industrial utility and, in order for this to be assessed systematically through screening experiments, the availability of a range of such ligands is required. To date, access to these ligands has been limited by the non-availability of suitable precursors. Through the provision of compound (1), this limitation no longer applies.

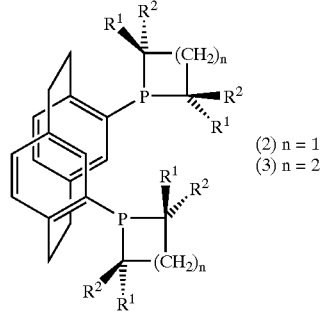

(2) n = 1
(3) n = 2

According to another aspect, this invention is based on investigation of chiral phosphonites and phosphorus diamides, ligands having a chiral backbone. Based on the ps-ortho disubstituted [2.2]-p-cyclophane skeleton, a new class of molecules is of general formula 4

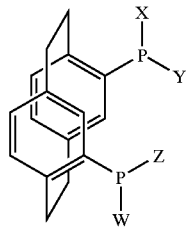

X,Y,Z,W = O:     4a *p*-cyclophane-phosphonites
X,Y,Z,W = N:     4b *p*-cyclophane-phosphorus-amides
X,Z = O; Y,W = N:   4c *p*-cyclophane-phosphonoamidite
X,Y,Z,W = Cl:    4d bis(dichlorophosphino)-*p*-cyclophane
X,Y,Z,W = H:     see formula 1

The most convenient synthesis of compounds 4a–c is based on the reaction of ps-ortho-bis(dichlorophosphino)-p-cyclophane 4d with the appropriate conjugate base pre-generated from a diol, diamine, amino-alcohol, alcohol or amine. Alternatively, compound 4d can be reacted with the appropriate diol, diamine, alcohol or amine in the presence of stoichiometric or catalytic amounts of a suitable base, for example a tertiary amine. Compound 4d can be obtained from the easily accessible precursor (S)-ps-ortho-dibromo-p-cyclophane (5) (D. J. Cram et al, *J. Am. Chem. Soc.* 1969, 3527) via different synthetic routes.

The ease of preparation of compounds 4a–c and the ready availability of the dioxo and diamido building blocks allows the generation of an unprecedented range of modifications based on the p-cyclophane backbone. In addition, the use of chiral chelating dialkoxo and di-amido substituents can enhance the chirality transfer in the catalytic process by means of a matching effect of the chirality of the backbone and the chirality of the heteroatom units. The use of monodentate alkoxo and amido ligands produces more flexible ligands that can complement the more rigid and sterically congested dialkoxo/di-amido ligands. Chiral phosphonites derived from monodentate alcohols or amines are completely unprecedented.

Chiral di-phosphonites and phosphorus diamides based on the ps-ortho disubstituted p-cyclophane skeleton are good ligands for transition metals, notably rhodium, iridium and ruthenium. Compounds 6–8 are specific examples of the above mentioned complexes.

| | |
|---|---|
| [(4a–c)Rh(COD)]BF$_4$ | 6a–c |
| [(4a–c)Ir(COD)]BF$_4$ | 7a–c |
| (4a–c)Ru(diamine)Cl$_2$ | 8a–c |

Using the most bulky chiral dialkoxo substituents, a very strong matching/mismatching effect was found in the formation of the metal complexes. Complexes 6–8 act as highly efficient catalysts for asymmetric reactions, notably asymmetric hydrogenation. They may also be used for asymmetric hydroformylation.

In particular, high levels of stereoselection are induced by rhodium complexes 6a of p-cyclophane phosphonites in the hydrogenation of dehydroaminoacids. These results match and in certain applications surpass the results reported for the known rhodium-phosphonites systems. Surprisingly, better results than in the literature are obtained in protic solvents; aprotic solvents give a noticeable increase in selectivity.

Further, the ruthenium complexes 8a of p-cyclophane-phosphonite 4a and a chiral diamine catalyse the reduction of non functionalised ketones and imines. While it is known that the reduction of ketones is catalysed by phosphine-ruthenium-diamine complexes (Noyori and Ohkuma, *Angew.Chem.Int.Ed.*, 2001, 40), the results here presented are unprecedented.

DESCRIPTION OF PREFERRED EMBODIMENTS

Compounds 4 of the invention may be prepared from enantiomerically pure ps-ortho-dihalogen-p-cyclophane 5 (X=Br). Phosphonites 4a can be obtained by direct metalation of 5 with a strong organometallic base and reaction with the appropriate chloro-phosphonite 9 (Scheme 1). An alternative and more convenient procedure involves the reaction of the novel intermediate ps-ortho-bis(dichlorophosphino)-p-cyclophane 4d with the appropriate alcohol or diol or their metal bases (also in Scheme 1).

Scheme 1

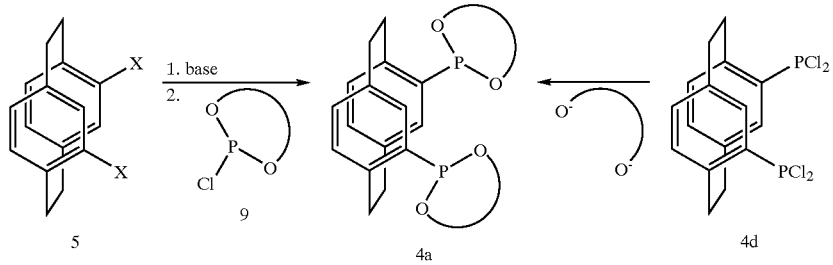

Compound 4d was found to be a convenient general intermediate, easy to prepare and to handle. It is best prepared by metalating the dibromo compound 5 (X=Br), followed by quenching with a chloro-phosphorus-diamide 10 such as, for example, ClP(NMe$_2$)$_2$ or ClP(i-Pr$_2$N)$_2$ (Scheme 2). Compounds 4b (R=Me, i-Pr) are transformed into compound 4d by treating them with an HCl solution (Et$_2$O or any other convenient solvent), either generated in situ or preformed (again, see Scheme 2).

Scheme 2

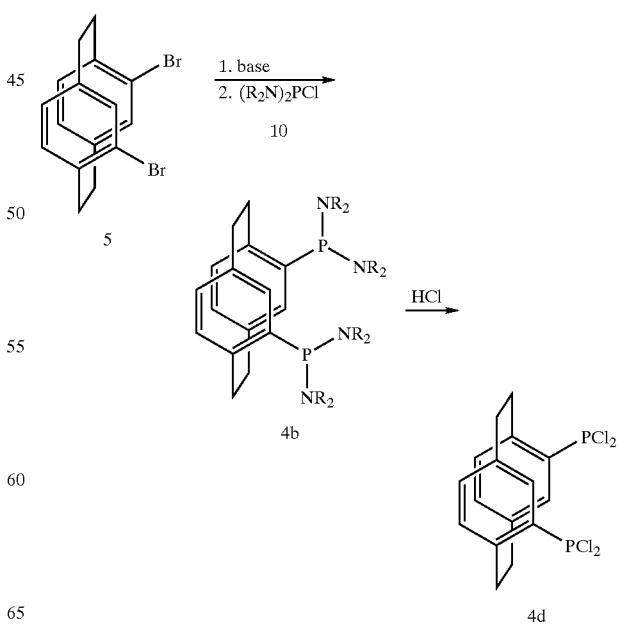

It is also possible to react compound 4b (R=Me, i-Pr) directly with a diol in presence of an appropriate base to produce phosphonites 4a (Buono et al, *Synlett* 1998, 49; van Boom et al, *Tetrahedron Let.* 2000, 8635—Scheme 3). The same procedure can be applied to the preparation of compounds 4b–c by reaction with an appropriate diamine or aminoalcohol.

Scheme 3

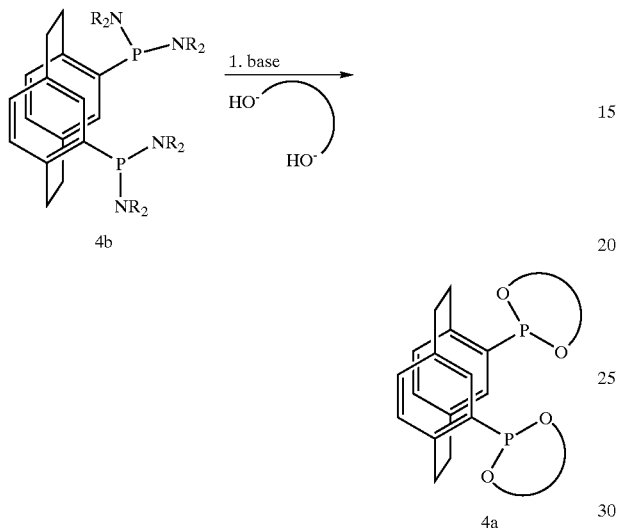

It has been found that the reaction of 4d with the conjugate base of a number of diols and alcohols proceeds smoothly at room temperature to provide the corresponding phosphonites 4a in good yields. All of them are relatively insoluble in MeOH and can be isolated from the reaction crude simply by removing the reaction solvent and washing with MeOH (the salts generated in the reaction being soluble in MeOH). Specific examples of compounds 4a are those were prepared from the alkoxo and di-alkoxo units 11–21, of which 11, 20 and 21 are achiral entities.

11

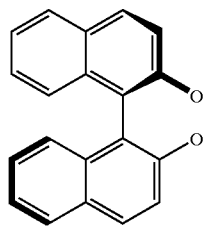

12

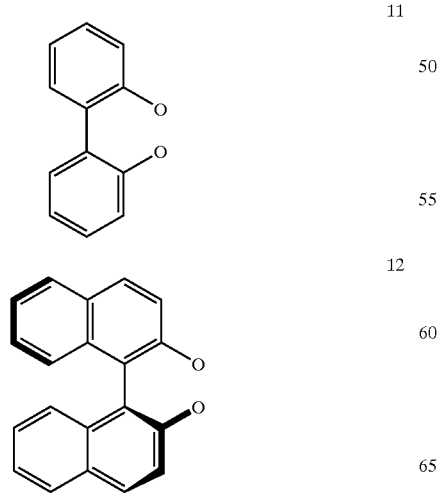

-continued

13

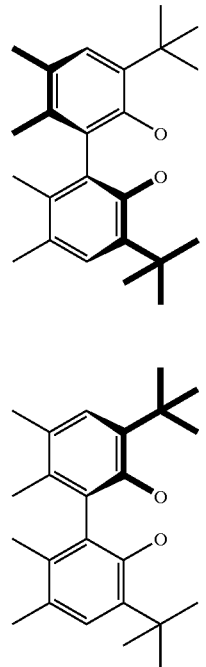

14

15

16

17

18

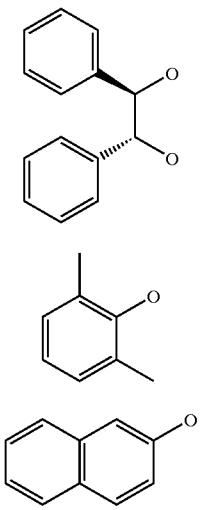

Examples of compounds 4b and 4c were prepared respectively from diamido units 22–25 and alkoxo-amido units 26–27.

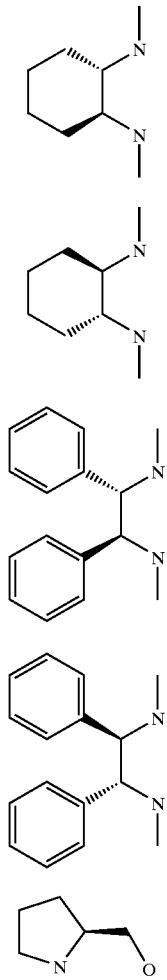

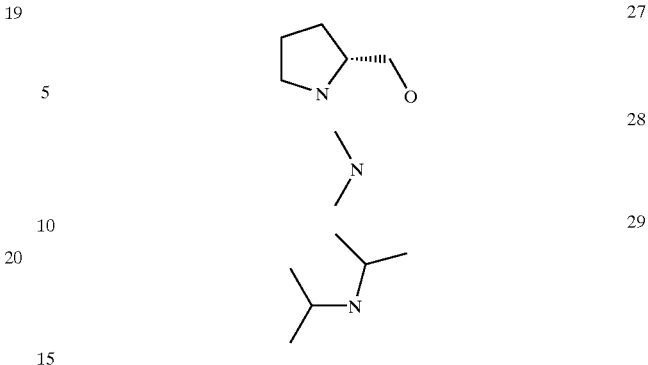

In compounds 4c, the fact that the phosphorus atom becomes a stereogenic center might produce the formation of a mixture of diastereoisomers. Nevertheless, spectroscopic evidences indicate that phosphonoamidite 4c/23 is formed as single diastereoisomer (Example 13). Compounds 4b/28 and 4b/29 were prepared as precursors for the synthesis of key intermediate 5. Compound 4d is also a very convenient intermediate for the synthesis of the diphosphine 1, by reduction with any of various reducing agents such as Red-Al or $LiAlH_4$.

Compounds 4a–c were found to be good ligands for transition metals (notably rhodium, iridium, ruthenium). The metal complexes 6a–c, 7a–c and 8a–c were generated according to standard procedures by reacting precursors such as $[(COD)_2Rh]BF_4$ and $[(COD)_2Ir]BF_4$, $[(benzene)RuCl_2]_2$. Other suitable metal-containing precursors can be used, according to the procedures known to those skilled in the art.

Unexpectedly, when phosphonites 4a/14 and 4a/15, bearing the most bulky dialkoxo substituents are used, a very strong matching/mismatching effect is found in the formation of the metal complexes. Only the ligand derived from (R)-15 and (S)-4d gave the desired Rh complex. The ligand derived from (S)-14 and (S)-4d did not react with $[(COD)_2Rh]BF_4$. This allows the use of the ligand as a diastereoisomeric mixture, selectively forming the metal complex derived from the matching (S)-4a/(R)-15 diastereoisomer. Conveniently a 1:1 mixture of 14 and 15 (racemic diol) may be used to prepare the said diastereoisomeric mixture. Alternatively, enantiomerically pure 14 or 15 can be combined with racemic 5.

The rhodium complexes 6a of phosphonites 4a display high activity and selectivity in the hydrogenation of dehydroaminoacids. These results match any other result reported for the known rhodium-phosphonites systems. Surprisingly, better results than in the literature (Reetz et al, *Tetrahedron:Asymmetry* 1999,2129) are obtained in protic solvents (e.g. MeOH); the use of aprotic solvents (e.g. toluene) produces a slight increase in selectivity. The stability of the catalysts in protic solvents (e.g. MeOH or $MeOH/H_2O$) increases the potential utility in the hydrogenation of molecules of pharmaceutical interest, which are often polar and water-soluble molecules.

The ruthenium complexes 8a containing ligands 4a and a chiral diamine such as DPEN (1,2-diphenyl-1,2-ethanediamine) catalyse the reduction of non-functionalised ketones and imines. The asymmetric reduction of imines is particularly important since only a few catalysts are known to efficiently promote this transformation.

The following Examples illustrate the invention. Examples 1 to 14 show the synthesis of the ligand precursors and ligands (Examples 3 and 4 illustrate alternative procedures, to give the same product). Examples 15 and 16 show the synthesis of complexes. Examples 17 to 22 are of hydrogenation. Example 23 relates to compound 1.

EXAMPLE 1

(S)-ps-ortho-Bis[bis(dimethylamino)phosphino]-[2.2]-p-cyclophane (S)-4b/28

(S)-ps-ortho-Dibromo-p-cyclophane (1.098 g, 3 mmol) was placed in a Schlenk flask under nitrogen atmosphere and dissolved in anhydrous $Et_2O$ (40 mL). The solution was then cooled to −78° C. in a dry ice/ethanol bath. A pentane solution of t-BuLi (1.7 M, 7.1 mL, 12 mmol) was added dropwise over five minutes. The reaction was stirred at −78° C. for 1 hour while $P(NMe_2)_3$ was placed in a Schlenk flask under nitrogen atmosphere and $PCl_3$ was slowly added at room temperature. The rate of addition was such that internal temperature did not raise above 30° C. The reaction was then diluted with anhydrous $Et_2O$ (10 mL) and stirred at room temperature for 30 minutes. The p-cyclophane lithium dianion solution was removed from the cooling bath and immediately quenched with the solution of $ClP(NMe_2)_2$. The reaction was diluted with more $Et_2O$ (15 mL) and allowed to reach room temperature over 30 minutes. Silica gel (~5 mL) was added and the reaction was stirred for further 20 minutes, then filtered over a sintered glass filter, under nitrogen atmosphere. The resulting clear colourless solution was evaporated under reduced pressure. The solid residue was redissolved in $Et_2O$ (10 mL) and added to MeOH (10 mL). Vacuum was applied to remove $Et_2O$ and a white solid precipitated. The solid was allowed to settle and the supernatant solution was removed, the solid was washed with more MeOH (10 mL) and dried under vacuum (0.52 g, 39% yield). The mother liquors were evaporated to dryness and the solid residue was treated as above with $Et_2O$ (5 mL) and MeOH (5 mL) to produce a second crop of product (overall yield: 74%, white crystalline powder). $^{31}P$ NMR (162 MHz, $C_6D_6$): 120.3 ppm.

EXAMPLE 2

(S)-ps-ortho-bis[bis(di-i-propylamino)phosphino]-[2.2]-p-cyclophane (S)-4b/29

(S)-ps-ortho-Dibromo-p-cyclophane (0.82 g, 2.24 mmol) was placed in a Schlenk flask under nitrogen atmosphere and dissolved in anhydrous $Et_2O$ (30 mL). The solution was then cooled to −78° C. in a dry ice/ethanol bath. A pentane solution of t-BuLi (1.7 M, 5.4 mL, 9.2 mmol) was added dropwise over five minutes. The reaction was stirred at −78° C. for 10 minutes, then the cooling bath was removed and the reaction stirred for further 40 minutes. Solid $(i-PrN)_2PCl$ (1.25 g, 4.68 mmol) was added in one portion and the reaction was stirred at room temperature for 30 minutes. Anhydrous MeOH (15 mL) was added, $Et_2O$ was removed under reduced pressure. The white solid that precipitated out of solution was collected on a sinthered glass filter under nitrogen and dried under vacuum (1.26 g, 84% yield). $^{31}P$ NMR (162 MHz, $C_6D_6$): 86.1 ppm.

EXAMPLE 3

(S)-ps-ortho-bis(dichlorophosphino)-[2.2]-p-cyclophane (S)-4d (S)-ps-ortho-bis[bis(dimethylamino)phosphino]-[2.2]-p-cyclophane (3.6 g, 8.1 mmol) was suspended in anhydrous $Et_2O$ (300 mL). The suspension was cooled to −78° C. in a dry ice/ethanol bath and anhydrous HCl was bubbled through the reaction to saturate it. The reaction was then allowed to warm up to room temperature over 1.5 hours. Nitrogen was bubbled through the reaction for 30 minutes. The salts were removed by filtration over a sintered glass filter under nitrogen. The solvent was evaporated; the solid white residue was washed with pentane (5 mL) and dried under vacuum to give the product as a white powder (2.07 g, 62% yield). $^{31}P$ NMR (162 MHz, $CDCl_3$): 169.2 ppm.

EXAMPLE 4

(S)-ps-ortho-bis(dichlorophosphino)-[2.2]-p-cyclophane (S)-4d

A solution of HCl in $Et_2O$ (2M, 50 mL, 100 mmol) was added to solid (S)-ps-ortho-bis[bis(di-i-propylamino) phosphino]-[2.2]-p-cyclophane (2.76 g, 4.12 mmol) at room temperature, under stirring. The reaction was stirred at room temperature for 18 hours, then the solvent was removed and the solid residue was suspended in $Et_2O$ (50 mL). Salts were removed by filtration. The solvent was removed, $Et_2O$ (20 mL) and hexane (40 mL) were added and the resulting cloudy solution was filtered. The solvent was removed, hexane was added (60 mL), the reaction was heated to 70° C. for 10 minutes, then the resulting cloudy solution was filtered to give a clear solution. The solvent was evaporated leaving the product as a white powder (0.95 g, 56% yield). $^{31}P$ NMR (162 M, $CDCl_3$): 169.2 ppm.

EXAMPLE 5

(S)-ps-ortho-bis(5,7-6-phosphadibenzo[a,c]cyclohepten-6-yl)-[2.2]-p-cyclophane (S)-4a/11 n-BuLi (2.5 M in hexane, 1.64 mL, 4.1 mmol) was added to a solution of 2,2'-biphenol (373 mg, 2 mmol) in anhydrous THF (15 mL). The reaction was stirred for 40 minutes at room temperature, then the solution was added dropwise to a solution of (S)-ps-ortho-bis(dichlorophosphino)-[2.2]-p-cyclophane 4d (410 mg, 1 mmol) in anhydrous THF (20 mL). The reaction was stirred at room temperature for 1 hour, then it was quenched by adding MeOH (1 mL). The solvent was removed under vacuum, anhydrous MeOH was added (10 mL). The resulting suspension was stirred for 10 minutes, then the solid was allowed to settle and the supernatant solution was removed. The procedure was repeated twice (2×5 mL MeOH), then the white solid residue was dried under vaccum (438 mg, 69% yield). $^{31}P$ NMR (162 MHz, $CDCl_3$): 194.2 ppm.

EXAMPLE 6

(S)-ps-ortho-bis{(R)-3,5-dioxa-4-phosphacyclohepta[2,1-a;3,4-a']dinaphthalen-4-yl}-[2.2]-p-cyclophane (S)-4a/13 n-BuLi (2.5 M in hexane, 0.82 mL, 2.05 mmol) was added to a solution of (R)-BINOL (286 mg, 1 mmol) in anhydrous THF (10 mL). The reaction was stirred for 30 minutes at room temperature, then the solution was added dropwise to a solution of (S)-ps-ortho-bis(dichlorophosphino)-[2.2]-p-cyclophane 4d (205 mg, 0.5 mmol) in anhydrous THF (15 mL). The reaction was stirred at room temperature for 30 minutes, then it was quenched by adding MeOH (2 mL). The solvent was concentrated under vacuum to about 2 mL, then anhydrous MeOH was added (10 mL). The resulting suspension was stirred for 10 minutes, the solid was allowed to settle and the supernatant solution was removed. The solid was washed with more MeOH following the same procedure (5 mL MeOH), then the white solid residue was dried under vacuum (200 mg, 48% yield). $^{31}$p NMR (162 MHz, $C_6D_6$): 217.6 ppm.

EXAMPLE 7

(S)-ps-ortho-bis{(S)-3,5-dioxa-4-phosphacyclohepta[2.1-a;3.4-a']dinaphthalen-4-yl}-[2.2]-p-cyclophane (S)-4a/12 n-BuLi (2.5 M in hexane, 0.82 mL, 2.05 mmol) was added to a solution of (S)-BINOL (286 mg, 1 mmol) in anhydrous THF (10 mL). The reaction was stirred for 30 minutes at room temperature, then the solution was added dropwise to a solution of (S)-ps-ortho-bis(dichlorophosphino)-[2.2]-p-cyclophane 4d (205 mg, 0.5 mmol) in anhydrous THF (15 mL). The reaction was stirred at room temperature for 30 minutes, then it was quenched by adding MeOH (2 mL). The solvent was concentrated under vacuum to about 2 mL, then anhydrous MeOH was added (20 mL). The resulting suspension was stirred for 10 minutes, the solid was allowed to settle and the supernatant solution was removed. The white solid residue was dried under vacuum (300 mg, 72% yield). $^{31}$p NMR (162 MHz, $C_6D_6$): 203.8 ppm.

EXAMPLE 8

(S)-ps-ortho-bis{(R)-di-t-butyl-1,2,10,11-tetramethyl-5,7-dioxa-6-phospha-dibenzo[a,c]cyclohepten-6-yl}-[2.2]-p-cyclophane (S)-4a/15 n-BuLi (2.5 M in hexane, 0.82 mL, 2.05 mmol) was added to a solution of (R)-3,3'-t-butyl-5,5',6,6'-dimethyl-2,2'-biphenol (286 mg, 1 mmol) in anhydrous THF (10 mL). The reaction was stirred for 1 hour at 45° C. minutes, then the solution was added dropwise over 40 minutes to a solution of (S)-ps-ortho-bis(dichlorophosphino)-[2.2]-p-cyclophane 4d (205 mg, 0.5 mmol) in anhydrous THF (20 mL) heated at 45° C. The reaction was stirred at 55° C. for 1.5 hours, the solvent was concentrated under vacuum to about 2 mL, then anhydrous MeOH was added (10 mL). The resulting suspension was stirred for 10 minutes, the solid was allowed to settle and the supernatant solution was removed. The solid was washed with more MeOH following the same procedure (5 mL MeOH), then the white solid residue was dried under vacuum (257 mg, 53% yield). $^{31}$p NMR (162 MHz, $C_6D_6$): 188.6 ppm.

EXAMPLE 9

(S)-ps-ortho-bis((S)-di-t-butyl-1,2,10,11-tetramethyl-5,7-dioxa-6-phospha-dibenzo[a,c]cyclohepten-6-yl)-[2.2]-p-cyclophane (S)-4a/14 n-BuLi (2.5 M in hexane, 0.82 mL, 2.05 mmol) was added to a solution of (S)-3,3'-t-butyl-5,5',6,6'-dimethyl-2,2'-biphenol (355 mg, 1 mmol) in anhydrous THF (10 mL). The reaction was stirred for 1 hour at 30° C. minutes, then the solution was added dropwise over 1 hour to a solution of (S)-ps-ortho-bis(dichlorophosphino)-[2.2]-p-cyclophane 4d (205 mg, 0.5 mmol) in anhydrous THF (20 mL) heated at 45° C. The reaction was stirred at 55° C. for 1 hour, the solvent was concentrated under vacuum to about 2 mL, then anhydrous MeOH was added (15 mL). The resulting suspension was stirred for 10 minutes, the solid was allowed to settle and the supernatant solution was removed. The solid was washed with more MeOH following the same procedure (2×15 mL MeOH), then the white solid residue was dried under vacuum (235 mg, 48% yield). $^{31}$p NMR (162 MHz, $C_6D_6$): 180.9 ppm.

EXAMPLE 10

(S)-ps-ortho-bis[di(2,6-dimethylphenoxy)phosphino]-[2.2]-p-cyclophane (S)-4a/20 n-BuLi (2.5 M in hexane, 0.32 mL, 0.8 mmol) was added to a solution of 2,6-dimethylphenol (98 mg, 0.8 mmol) in anhydrous THF (5 mL). The reaction was stirred at room temperature for 15 minutes, then the solution was added to a solution of (S)-ps-ortho-bis(dichlorophosphino)-[2.2]-p-cyclophane 4d (73 mg, 0.18 mmol) in anhydrous THF (5 mL). The reaction was stirred at room temperature for 30 minutes, then the solvent was evaporated. $Et_2O$ (15 mL) and $SiO_2$ (~2 mL) were added and the reaction was filtered to get a clear solution. The solvent was concentrated to ~1 mL and anhydrous MeOH (2 mL) was added. The resulting suspension was stirred for 10 minutes, the solid was allowed to settle and the supernatant solution was removed. The resulting white solid residue was dried under vacuum (yield not calculated). $^{31}$P NMR (162 MHz, $C_6D_6$): 186.3 ppm.

EXAMPLE 11

(S)-ps-ortho-bis[di(2-naphthoxy)phosphino]-[2.2]-p-cyclophane (S)-4a/21

(S)-ps-ortho-Dibromo-p-cyclophane (366 mg, 1 mmol) was placed in a Schlenk flask under nitrogen atmosphere and dissolved in anhydrous $Et_2O$ (30 mL). The solution was then cooled to −78° C. in a dry ice/ethanol bath. A pentane solution of t-BuLi (1.5 M, 2.75 mL, 4.1 mmol) was added dropwise. The cooling bath was removed and the reaction was allowed to warm up. After 30 minutes a solution of O,O'-bis(2-naphthyl)chlorophosphine (775 mg, 2.2 mmol) in $Et_2O$ (10 mL) was added. The reaction was stirred at room temperature for further 90 minutes, then quenched with anhydrous MeOH (1 mL). The solvent was evaporated and the solid residue was re-dissolved in anhydrous $Et_2O$ (10 mL) and MeOH (10 mL). The solvent was concentrated under reduced pressure to ~5 mL and the resulting white precipitate was allowed to settle. The supernatant solution was removed. The solid was washed with more MeOH (10 mL) following the same procedure, then the white solid residue was dried under vacuum (275 mg, 33% yield). $^{31}$P NMR (162 MHz, $C_6D_6$): 178.0 ppm.

EXAMPLE 12

(S)-ps-ortho-bis{(4S,5S)-2.2-Dimethyl-4,4,8,8-tetraphenyltetrahydro-[1,3]-dioxolo[4,5-e][1,3,2]dioxaphosphepin-6-yl}-[2.2]-p-cyclophane (S-4a/16 n-BuLi (2.5 M in hexane, 0.45 mL, 1.1 mmol) was added to a solution of (4S,5S)-4,5-bis(diphenylhydroxymethyl)-2,2-dimethyldioxolane (=TADDOL)(235 mg, 0.5 mmol) in anhydrous THF (4 mL). The reaction was stirred for 1 hour at room temperature, then the yellow solution was added dropwise over 1 min to a solution of (S)-ps-ortho-bis(dichlorophosphino)-[2.2]-p-cyclophane 4d (100 mg, 0.25 mmol) in anhydrous THF (5 mL) at room temperature. The reaction was stirred at room temperature for 1 hour, the solvent concentrated to dryness under vacuum and anhydrous MeOH was added (3 mL). The resulting suspension was allowed to settle and the supernatant solution was removed. The solid was washed with more MeOH following the same procedure (3 mL) and the white solid residue was dried under vacuum (yield not calculated). $^{31}$P NMR (162 MHz, $C_6D_6$): 184.9.

EXAMPLE 13

(S)-ps-ortho-bis{(S)-tetrahydropyrrolo[1,2-c][1,3,2] oxaphophol-1-yl}-p-cyclophane (S)-4c/26 n-BuLi (2.5 M in hexane, 0.84 mL, 2.1 mmol) was added to a solution of (S)-prolinol (106 mg, 1.05 mmol) in anhydrous THF (10 mL) at −78° C. The reaction was stirred at −78° C. for 10 minutes, then the solution was added to a solution of(S)-ps-ortho-bis(dichlorophosphino)-[2.2]-p-cyclophane 4d (205 mg, 0.5 mmol) in anhydrous THF (10 mL). The reaction was stirred at room temperature for 1 hour, then the solvent was evaporated. Anhydrous THF (1 mL) and MeOH (15 mL) were added. The resulting suspension was stirred for 10 minutes, the solid was allowed to settle and the supernatant solution was removed. The solid was washed with more MeOH (5 mL) following the same procedure, then the white solid residue was dried under vacuum (100 mg, 45% yield). $^{31}$P NMR (162 MHz, CDCl$_3$): 159.0 ppm.

EXAMPLE 14

(S)-ps-ortho-bis{(4R,5R)-1,3-Dimethyloctahydrobenzo[1,3,2]diaza-phospholyl)-[2.2]-p-cyclophane (S)-4b/23 n-BuLi (2.5 M in hexane, 0.9 mL, 2.3 mmol) was added to a solution of (1R,2R)-1,2-(N,N'-diaminomethyl-cyclohexane) (155 mg, 1.1 mmol) in anhydrous THF (6 mL) and the deep red solution was stirred for 1 hour at room temperature (precipitation of a red solid was observed). A solution of (S)-ps-ortho-bis(dichlorophosphino)-[2.2]-p-cyclophane 4d (210 mg, 0.5 mmol) in anhydrous THF (8 mL) was added to the previous suspension at room temperature. The reaction was stirred for 1 hour, the solvent concentrated to dryness under vacuum and anhydrous MeOH was added (5 mL). The resulting suspension was allowed to settle and the supernatant solution was removed. The solid was washed with more MeOH following the same procedure (5 mL), then the pale yellow solid residue was dried under vacuum (yield not calculated). $^{31}$P NMR (162 MHz, C$_6$D$_6$): 132.4 ppm.

EXAMPLE 15

General Procedure for the Synthesis of Cationic Rhodium Complexes 6a

Ligand 4a (1.05 mmol) and [(COD)$_2$Rh]BF$_4$ (1 mmol) were dissolved in anhydrous DCM (5–10 mL) and the reaction was stirred at room temperature for 2–16 hours. The solvent was concentrated under vacuum to about 0.5 mL and anhydrous Et$_2$O (5–15 mL) was added. The resulting yellow suspension was stirred at room temperature for 10–30 minutes, the solid was allowed to settle and the supernatant solution was removed. The solid residue was washed following the same procedure with more Et$_2$O (2×5 mL) and dried under vacuum.

$^{31}$P NMR (162 MHz, CDCl$_3$): (S)-6a/11: 186.3 ppm (d), (S)-6a/12: 177.0 ppm (d), (S)-6a/13: 186.1 ppm (d), (S)-6a/15: 174.3 ppm (d), (S)-6a/16: 142.0 ppm (d).

EXAMPLE 16

Ruthenium Complexes 8a

[RuCl$_2$C$_6$H$_6$]$_2$ (0.06 mmol) and ligand 4a (0.11 mmol) were placed in a dry Schlenk flask under a nitrogen atmosphere. To the solids was added dry degassed DMF (1 mL) and the reaction vessel was evacuated and then repressurised with nitrogen gas. This was repeated four times. The Schlenk flask containing the heterogeneous mixture was placed in an oil bath at 100° C. and stirring was applied for 3.5 hour. The homogeneous mixture was allowed to cool to room temperature and then (RR)-DPEN (=1,2-diphenyl-1,2-ethanediamine) (0.12 mmol) was added. The mixture was stirred for 66 h at room temperature, then evaporated under high vacuum providing a solid. This was washed with dichlormethane (3 mL) and the solvent was evaporated. This process was repeated providing a tan-brown coloured powder.

$^{31}$P NMR (162 MHz, CDCl$_3$): (S)-8a/11: 222.4 ppm, (S)-8a/13: 223.5 ppm.

EXAMPLES 17 to 20

All hydrogenations were carried out in a 50 mL Parr hydrogenation vessel equipped with an injection port with a rubber septum for the addition of the solvent using a syringe, a pressure gauge, a tightly fitting removable internal glass liner, a magnetic stirring bar. HPLC grade solvents ware degassed prior to the use by bubbling nitrogen for at least 30 minutes.

Substrate (2 mmol) and catalyst 6a (0.002 mmol) were placed in the hydrogenation vessel that was subsequently closed and flushed with nitrogen. The vessel was purged with hydrogen by pressurising to 5 bar and then releasing the pressure. This procedure was repeated at least four times. The solvent (5 mL) was added through the injection port and the reaction was purged again with hydrogen. It was then pressurised to 3.5 bar and stirred at room temperature. The reaction was stopped when no more hydrogen uptake was detected on the pressure gauge. A crude reaction sample was diluted in MTBE and analysed by GC (DexCB chiral column, the free acid was derivatised by adding an excess of trimethylsilyl diazomethane) for conversion and selectivity.

EXAMPLE 17

Hydrogenation of Methyl Acetamidoacrylate

| Catalyst | Diol component of the ligand | Solvent | Time (h) | Conv. (%) | Ee (%) |
|---|---|---|---|---|---|
| (S)-6a/11 | biphenol | MeOH | 0.5 | >99 | 89 (S) |
| (S)-6a/13 | (R)-BINOL | MeOH | 0.5 | >99 | 99 (S) |
| (S)-6a/12 | (S)-BINOL | MeOH | 1 | ~2 | — |
| (S)-6a/12 | (S)-BINOL | MeOH | 16 | 98 | 74 (S) |
| (S)-6a/15 | (R)-BIPHEN | MeOH | 21 | 25 | 46 (S) |
| (S)-6a/11 | biphenol | MeOH/H$_2$O 9/1 | 3 | >99 | 96 (S) |
| (S)-6a/11 | biphenol | DCM | 1 | >99 | 98 (S) |
| (S)-6a/11 | biphenol | Toluene | 0.5 | >99 | 99 (S) |
| (S)-6a/21 | naphthol* | MeOH | 15 | >99 | 37 (R) |
| (S)-6a/21 | naphthol* | Toluene | 15 | 80 | 31 (R) |

*monodentate component

EXAMPLE 18

Hydrogenation of Acetamidoacrylic Acid $$\underset{\text{NHAc}}{\overset{\text{COOH}}{\diagup\!\!\!\diagup}} \xrightarrow[\text{RT, 3.5 bar H}_2]{[(4a)Rh(COD)]BF_4\ 0.1\%} \underset{\text{NHAc}}{\overset{\text{COOH}}{\diagup}}$$

| Catalyst | Diol component of the ligand | Solvent | Time (h) | Conv. (%) | Ee (%) |
|---|---|---|---|---|---|
| (S)-6a/13 | (R)-BINOL | MeOH | 0.5 | >99 | 97 (S) |

EXAMPLE 19

Hydrogenation of Acetamidocinnamic Acid $$\underset{\text{Ph}}{\overset{\text{COOH}}{\diagup\!\!\!\diagup}}\!\!\text{NHAc} \xrightarrow[\text{RT, 3.5 bar H}_2]{[(4a)Rh(COD)]BF_4\ 0.1\%} \underset{\text{Ph}}{\overset{\text{COOH}}{\diagup}}\!\!\text{NHAc}$$

| Catalyst | Diol component of the ligand | Solvent | Time (h) | Conv. (%) | Ee (%) |
|---|---|---|---|---|---|
| (S)-6a/11 | biphenol | MeOH | 0.5 | >99 | 93 |
| (S)-6a/13 | (R)-BINOL | MeOH | 0.5 | >99 | 99 |

EXAMPLE 20

Hydrogenation of Methyl Acetamidocinnamate $$\underset{\text{Ph}}{\overset{\text{COOCH}_3}{\diagup\!\!\!\diagup}}\!\!\text{NHAc} \xrightarrow[\text{RT, 3.5 bar H}_2]{[(4a)Rh(COD)]BF_4\ 0.1\%} \underset{\text{Ph}}{\overset{\text{COOCH}_3}{\diagup}}\!\!\text{NHAc}$$

| Catalyst | Diol component of the ligand | Solvent | Time (h) | Conv. (%) | Ee (%) |
|---|---|---|---|---|---|
| (S)-6a/11 | biphenol | MeOH | 0.5 | >99 | 95 (S) |
| (S)-6a/13 | (R)-BINOL | MeOH | 0.5 | >99 | 97 (S) |
| (S)-6a/13 | (R)-BINOL | toluene | 2 | >99 | 99 (S) |

EXAMPLE 21

Hydrogenation of Methyl Acetamidocinnamate at Reduced Catalyst Loadings

Substrate (10 mmol) and catalyst 6a (0.002 mmol) were placed in the hydrogenation vessel that was subsequently closed and purged with nitrogen by pressurising to 5 bar and releasing the pressure. The procedure was repeated three times. The vessel was subsequently purged with hydrogen by pressurising to 5 bar and then releasing the pressure. This procedure was repeated at least four times. The solvent (5 mL) was added through the injection port and the reaction was purged again with hydrogen. It was then pressurised to 5 bar and stirred at room temperature. The reaction was refilled with hydrogen in order to maintain the pressure between 5 and 3.5 bar. The reaction was stopped when no more hydrogen uptake was detected on the pressure gauge. A crude reaction sample was diluted in MTBE and analysed by $^1$H NMR for conversion and by GC (DexCB chiral column) for selectivity.

$$\underset{\text{Ph}}{\overset{\text{COOCH}_3}{\diagup\!\!\!\diagup}}\!\!\text{NHAc} \xrightarrow[\text{RT, 3.5 bar H}_2]{[(4a)Rh(COD)]BF_4\ 0.02\%} \underset{\text{Ph}}{\overset{\text{COOCH}_3}{\diagup}}\!\!\text{NHAc}$$

| Catalyst | Diol component of the ligand | Solvent | Time (h) | Conv. (%) | Ee (%) |
|---|---|---|---|---|---|
| (S)-6a/11 | biphenol | MeOH | 0.5 | >99 | 95 (S) |
| (S)-6a/13 | (R)-BINOL | MeOH | 0.5 | >99 | 98.5 (S) |

EXAMPLE 22

Imine Hydrogenation with Catalyst 8a

N-(1-Phenylethylidene)aniline (1 mmol) and the catalyst were placed in the hydrogenation vessel that was subsequently closed and flushed with nitrogen. The vessel was purged with hydrogen by pressurising to 20 bar and then releasing the pressure. This procedure was repeated at least four times. 2-Propanol (4 mL) was added through the injection port and the reaction was purged again with hydrogen five times. The pressure was released and 1 M potassium tert-butoxide in tert-butanol (0.1 mmol) was added and the reaction was purged again with hydrogen four times. The reaction was pressurised to 15 bar and stirred at 65° C. for 20.5 h. A crude reaction sample was diluted in acetone and analysed by GC (DexCB chiral column) for conversion and selectivity.

$$\underset{\text{Ph}}{\overset{\text{N}^{\diagup\text{Ph}}}{\diagdown\!\!\!\diagdown}} \xrightarrow[\substack{65°\text{ C., H}_2\text{, 2-propanol,}\\ \text{potassium tert-butoxide}}]{[(4a)RuCl_2(R,R)DPEN]} \underset{\text{Ph}}{\overset{\text{HN}^{\diagup\text{Ph}}}{\diagdown}}\!\!\text{NHAc}$$

| Catalyst (amount) | Diol component of the ligand | Equivalents t-BuOK | Pressure (bar) | Time (h) | Conv. (%) | Ee (%) |
|---|---|---|---|---|---|---|
| (S)-8a/11 (1%) | biphenol | 0.1 | 15 | 20.5 | 88 | 62 |
| (S)-8a/11 (1%) | biphenol | 1 | 15 | 20 | 91 | 64 |
| (S)-8a/11 (0.1%) | biphenol | 0.1 | 20 | 69 | 100 | 72 |

EXAMPLE 23

(S)-ps-ortho-Diphosphino-[2.2]-p-cyclophane 1
Method A:

A 100 mL Schlenck flask equipped with a stirring bar was dried with heating and then filled with nitrogen. To this was added (S)-ps-ortho-bis(dichlorophosphino)-[2.2]-p-cyclophane (4d, Example 4: 300 mg, 0.75 g) and dry, degassed toluene (4 mL). The resulting solution was put in an oil bath at 50° C. and allowed to stabilize at that temperature for 5 min. A solution of Red-Al (65% wt solution in toluene, 1.9 mL, 8.0 mmol) was added over 2 min. The solution, which rapidly turned red, was well stirred for 2 hrs. After cooling down to room temperature, aqueous hydrochloric acid (2M, 5 mL) was slowly added, whereby vigorous gas evolution was observed. The upper, organic layer was transferred via cannula to a similarly dried 100 mL Schlenck flask equipped with a stirring bar. The aqueous phase is further extracted with toluene (2×4 mL) and transferred to the second Schlenck flask. The mixed organic layers are evaporated to dryness under reduced pressure with gentle heating to furnish a yellow oil comprising mainly the desired product; $^1$H NMR(400 MHz, C$_6$D$_6$): 2.3–2.7 (m, 3H); 3.0–3.1 (m, 1H); 3.55 and 3.75 (2d, $^1$J=200, $^2$J=12.6, 2H); 6.7–7.0 (m, 3H); $^{31}$P NMR (162 MHz, C$_6$D$_6$): −113.4 (t of d, $^1$J=200, $^3$J 7.9).

Method B:

A solution of ps-ortho-bis(dichlorophosphino)-[2,2]-p-paracyclophane (4d, 1.5 g, 3.65 mmol) in anhydrous THF (6 mL) was cooled to 0° C. A solution of LiAlH$_4$ in Et$_2$O (1M, 30 mL, 30 mmol) was added at 0° C. and the reaction mixture was stirred for 30 hours and allowed to reach room temperature during this time. It was then cooled again to 0° C. and degassed H$_2$O (3 mL) was added dropwise over 1 hour. The reaction mixture was evaporated to dryness under reduced pressure and the solid residue triturated with CH$_2$Cl$_2$, 5 mL×3). The solvent was removed under reduced pressure to give the product as a yellow solid (0.76 g, 76% yield).

We claim:

1. A compound of the following formula:

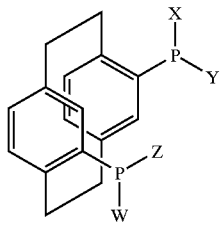

X, Y, Z, W=O: p-cyclophane-phosphonites
X, Y, Z, W=N: p-cyclophane-phosphorus-amides
X, Z=O; Y, W=N: p-cyclophane-phosphonoamidite
X, Y, Z, W=Cl: bis(dichlorophosphino)-p-cyclophane
X, Y, Z, W=H: ps-ortho-diphosphino-[2.2]-p-cyclophane
wherein each of W, X, Y and Z is a substituent selected from the group consisting of a conjugate base of a diol, a conjugate base of a primary or secondary diamine, and a conjugate base of an aminoalcohol, where a heteroatom is bonded to phosphorus, optionally linked in pairs X/Y and Z/W to form a ring, or W=X=Y=Z=H wherein a heteroatom is selected from the group consisting of halogens, nitrogen, oxygen and sulphur.

2. The compound according to claim 1, wherein the pair of substituents X/Y is the same as pair Z/W.

3. The compound according to claim 1, wherein W, X, Y and Z each include a heteroatom selected from the group consisting of halogens, nitrogen, oxygen and sulphur.

4. The compound according to claim 3, wherein the heteroatom is oxygen.

5. The compound according to claim 3, wherein the heteroatom is nitrogen.

6. The compound according to claim 3, wherein in each pair of substituents X/Y and Z/W the heteroatoms in each substituent are oxygen and nitrogen.

7. The compound according to claim 1, which is chiral and enantiomerically enriched.

8. The compound according to claim 1, wherein the diol is an enantiomerically enriched chiral diol.

9. The compound according to claim 8, wherein the chiral diol is a biaryl diol with axial chirality.

10. The compound according to claim 1, wherein the diamine is an enantiomerically enriched chiral primary or secondary diamine.

11. The compound according to claim 1, wherein the aminoalcohol is an enantiomerically enriched chiral aminoalcohol.

12. The compound according to claim 7, wherein the enantiomeric enrichment is at least 80%.

13. The compound according to claim 12, wherein the enantiomeric enrichment is at least 90%.

14. The compound according to claim 1, wherein the diol is achiral.

15. The compound according to claim 1, wherein X=Y=Z=W=Cl.

16. The compound according to claim 1, which is ps-ortho-diphosphino-[2.2]-p-cyclophane

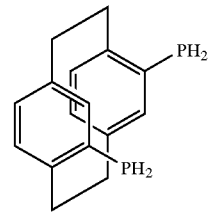

17. The compound according to claim 16, in enantiomerically enriched form.

18. The compound according to claim 17, in at least 80% enantiomerical excess.

19. The compound according to claim 17, in at least 95% enantiomerical excess.

20. A method for preparing a chiral ligand having the following structure:

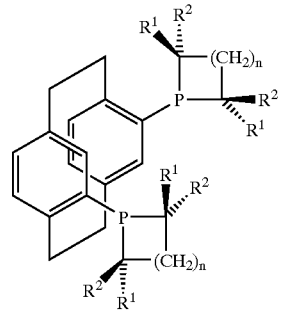

wherein R1 and R2 represent H or alkyl and n is 1, or 2 comprising using the following compounds:

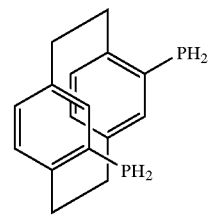

a reagent in preparing the chiral ligand.

21. A complex of an enantiomerically enriched compound of the following formula:

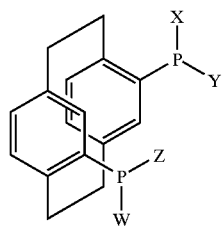

X, Y, Z, W=O: p-cyclophane-phosphonites
X, Y, Z, W=N: p-cyclophane-phosphorus-amides
X, Z=O; Y, W=N: p-cyclophane-phosphonoamidite
X, Y, Z, W=Cl: bis(dichlorophosphino)-p-cyclophane
X, Y, Z, W=H: ps-ortho-diphosphino-[2.2]-p-cyclophane
wherein each of W, X, Y and Z is a substituent selected from the group consisting of a conjugate base of a diol, a conjugate base of a primary or secondary diamine, and a conjugate base of an aminoalcohol, where a heteroatom is bonded to phosphorus, optionally linked in pairs X/Y and Z/W to form a ring, or W=X=Y=Z=H; wherein said compound is complexed with a transition metal, and enantiomerically enriched ligand and counterion necessary to complete the coordination sphere of the metal, wherein a heteroatom is selected from the group consisting of halogens, nitrogen, oxygen and sulphur.

22. The complex according to claim 21, wherein the transition metal is rhodium, iridium or ruthenium.

23. The complex according to claim 21 wherein the heteroatom is nitrogen.

24. The complex according to claim 21, wherein in each pair of substituents X/Y and Z/W the heteroatoms in each substituent are oxygen and nitrogen.

25. The complex according to claim 21, of the formula

[enantiomerically enriched compound)(diene)metal]Q wherein the metal is rhodium or iridium, the diene is 1.5-Cyclooctadiene or 2.5-Norbornadiene, and Q is BF4 or PF6.

26. The complex according to claim 25, wherein the metal is rhodium, the diene is 1.5-Cyclooctadiene, and Q is BF4.

27. The complex according to claim 25, wherein the metal is iridium, the diene is 1.5-Cyclooctadiene, and Q is BF4.

28. The complex according to claim 21, of the formula

[enantiomerically enriched compound)(diamine)metal(hal)2]

wherein the metal is ruthenium, hal is a halogen atom, and the diamine is an enantiomerically enriched chiral diamine.

29. A method for the preparation of a compound having the following formula:

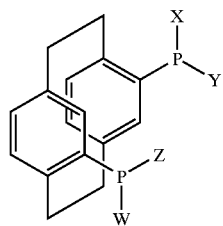

wherein each of W, X, Y, and Z is a substituent selected from the group consisting of a conjugate base of a diol, a conjugate base of a primary or secondary diamine, and a conjugate base of an aminoalcohol, where a heteroatom is bonded to phosphorus and wherein the pairs of substituents X/Y and Z/W are each the conjugate base of a diol; wherein said method comprises reacting, with the conjugate base of an alcohol or a diol, a compound having the following structure:

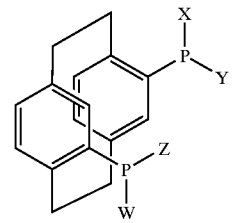

wherein each of W, X, Y and Z is a substituent selected from the group consisting of a conjugate base of a diol, a conjugate base of a primary or secondary diamine, and a conjugate base of an aminoalcohol, wherein a heteroatom is bonded to phosphorous, optionally linked in pairs X/Y and Z/W to form a ring and wherein each of W, X, Y and Z include a heteroatom selected from the group consisting of halogens, nitrogen, oxygen and sulphur.

30. A method for the preparation of a compound having the following formula:

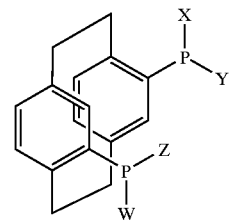

wherein each of W, X, Y, and Z is a substituent selected from the group consisting of a conjugate base of a diol, a conjugate base of a primary or secondary diamine, and a conjugate base of an aminoalcohol, where a heteroatom is bonded to phosphorus and wherein the heteroatom is nitrogen; wherein said method comprises reacting, with the conjugate base of an amine or diamine, a compound with the following structure:

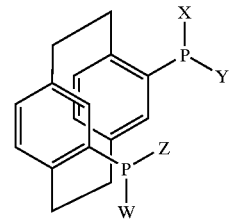

wherein each of W, X, Y and Z is a substituent selected from the group consisting of a conjugate base of a diol, a conjugate base of a primary or secondary diamine, and a conjugate base of an aminoalcohol, wherein a heteroatom is bonded to phosphorous, optionally linked in pairs X/Y and Z/W to form a ring and wherein each of W, X, Y and Z include a heteroatom selected from the group consisting of halogens, nitrogen, oxygen and sulphur.

31. A method for the preparation of a compound having the following formula:

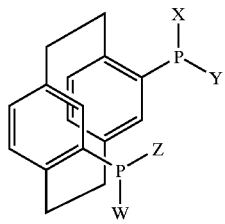

wherein each of W, X, Y, and Z is a substituent selected from the group consisting of a conjugate base of a diol, a conjugate base of a primary or secondary diamine, and a conjugate base of an aminoalcohol, where a heteroatom is bonded to phosphorus and wherein in each pair of substituents X/Y and Z/W the heteroatoms are oxygen and nitrogen; wherein said method comprises reacting, with the conjugate base of an amino alcohol, a compound having the following structure:

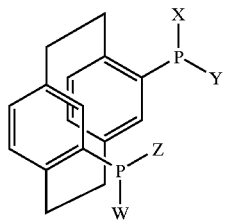

wherein each of W, X, Y and Z is a substituent selected from the group consisting of a conjugate base of a diol, a conjugate base of a primary or secondary diamine, and a conjugate base of an aminoalcohol, wherein a heteroatom is bonded to phosphorous, optionally linked in pairs X/Y and Z/W to form a ring and wherein each of W, X, Y and Z include a heteroatom selected from the group consisting of halogens, nitrogen, oxygen and sulphur.

32. A method for catalyzing an asymmetric process comprises using a complex of an enantiomerically enriched compound of the following formula:

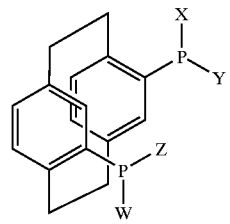

wherein each of W, X, Y and Z is a substituent selected from the group consisting of a conjugate base of a diol, a conjugate base of a primary or secondary diamine, and a conjugate base of an aminoalcohol, where a heteroatom is bonded to phosphorus, optionally linked in pairs X/Y and Z/W to form a ring, or W=X=Y=Z=H; wherein said compound is complexed with a transition metal, and an enantiomerically enriched ligand and counterion necessary to complete the coordination sphere of the metal, wherein a heteratom is selected from the group consisting of halogens. nitrogen. oxygen and sulphur.

33. The method according to claim 32, wherein the asymmetric process is hydrogenation.

34. The method according to claim 33, wherein the hydrogenation is of a C=C, C=N or C=O double bond.

35. The method according to claim 33, wherein the transition metal is rhodium, iridium or ruthenium.

36. The method according to claim 35, wherein the complex is of the formula

[enantiomerically enriched compound)(diene)metal]Q wherein the metal is rhodium or iridium, the diene is 1.5-Cyclooctadiene or 2.5-Norbornadiene, and Q is BF4 or PF6.

37. The method according to claim 33, wherein the hydrogenation is of a C=N or C=O double bond and the complex is of the formula

[enantiomerically enriched compound)(diamine)metal(hal)2]

wherein the metal is ruthenium, hal is a halogen atom, and the diamine is an enantiomerically enriched chiral diamine.

38. The method according to claim 32, wherein the asymmetric process is hydroformylation.

* * * * *